United States Patent
Winterfeld et al.

[11] Patent Number: 6,156,918
[45] Date of Patent: Dec. 5, 2000

[54] PROCESS FOR THE PREPARATION OF SILANES, WITH A TERTIARY HYDROCARBON GROUP IN THE A-POSITION RELATIVE TO THE SILICON ATOM

[75] Inventors: Joern Winterfeld; Bors Cajus Abele, both of Burghausen, Germany

[73] Assignee: Wacker-Chemie GmbH, München, Germany

[21] Appl. No.: 09/363,684

[22] Filed: Jul. 29, 1999

[30] Foreign Application Priority Data

Aug. 20, 1998 [DE] Germany .......................... 198 37 906

[51] Int. Cl.[7] .................................. C07F 7/08; C07F 7/10
[52] U.S. Cl. ............................................. 556/480; 556/415
[58] Field of Search ...................... 556/480, 415

[56] References Cited

U.S. PATENT DOCUMENTS

| | | | |
|---|---|---|---|
| 5,294,727 | 3/1994 | Kubota et al. .................. | 556/480 |
| 5,332,853 | 7/1994 | Morrison et al. . | |
| 5,872,274 | 2/1999 | Cannady et al. ............... | 556/480 |

FOREIGN PATENT DOCUMENTS

| | | |
|---|---|---|
| 0 177 454 A2 | 4/1986 | European Pat. Off. . |
| 0 405 560 A2 | 1/1991 | European Pat. Off. . |
| 0 542 250 A1 | 5/1993 | European Pat. Off. . |
| 0 656 363 A1 | 6/1995 | European Pat. Off. . |

OTHER PUBLICATIONS

Derwent Abstract corr. to EP 0 177 454 A2 AN 1986–095772, Apr. 1986.
"Tetrahedron Letters", vol. 30, No. 46, 1989, pp. 6393–6394.

Primary Examiner—Paul F. Shaver
Attorney, Agent, or Firm—Brooks & Kushman P.C.

[57] ABSTRACT

The invention relates to a process for the preparation of silanes of the general formula 1

$$R_m R^1_n SiX_{4-m-n} \quad (1)$$

by reaction of Grignard reagents of the general formula 2

$$R^1 MgX^1 \quad (2)$$

with silanes of the general formula 3

$$R_m SiX_{4-m} \quad (3)$$

wherein
  R denotes $C_1$- to $C_{10}$-hydrocarbon radicals optionally substituted by fluorine, chlorine or cyano radicals,
  $R^1$, in the α-position relative to the silicon atom, denotes tertiary $C_4$- to $C_{30}$-hydrocarbon radicals optionally substituted by fluorine, chlorine or cyano radicals,
  X and $X^1$ each denote chlorine, bromine or iodine,
  m denotes the values 2 or 3 and
  n denotes the values 1 or 2,
in the presence of a transition metal catalyst and an inert, aprotic, and chelating compound.

20 Claims, No Drawings

PROCESS FOR THE PREPARATION OF SILANES, WITH A TERTIARY HYDROCARBON GROUP IN THE A-POSITION RELATIVE TO THE SILICON ATOM

TECHNICAL FIELD

The invention relates to a process for the preparation of silanes with a tertiary hydrocarbon group in the α-position relative to the silicon atom.

BACKGROUND ART

In the tertiary hydrocarbon-containing class of silanes, the thexyl- and tert-butyl-substituted silanes are certainly the most investigated and most used silanes of this class. Thexyl-substituted silanes are in principle accessible via hydrosilylation reactions between an Si-H compound and 2,3-dimethyl-2-butene. Such a synthesis is described in EP-A-177 454. However, undesirable by-products, some of which are difficult to remove, occur in these reactions due to migration of the double bond.

A. Shirata, TETRAHEDRON LETT. 30 (1989) p. 6393, describes the preparation of tert-butyl-substituted silanes by reaction of halogenosilanes with tert-butylmagnesium chloride, catalysts being necessary to effect the reaction.

U.S. Pat. No. 5,332,853 describes the synthesis of tert-butylsilanes starting from tert-butyllithium. Although this reaction proceeds with quite good yields, it is of little economic interest because of the high price of the lithium alkyl. Furthermore, handling of pyrophoric tert-butyllithium, even in a highly dilute solution is extremely expensive and difficult on an industrial scale for safety reasons.

Various metal salts have been tested for their catalytic activity in increasing the yield in reactions of the cheaper metal alkyl, tertbutylmagnesium Grignard, with halogenosilanes to give the corresponding tertbutylsilanes. According to EP-A-405 560, satisfactory results were achieved with cyanide- or thiocyanate-containing catalysts such as silver cyanide, mercury(II) cyanide, copper(I) cyanide, sodium thiocyanate or copper(I) thiocyanate, but these involve major safety, environmental and disposal problems. In addition, the silanes prepared via cyanides and thiocyanates usually have an unpleasant smell, which can reduce the quality or capacity for use of the corresponding silane.

When more acceptable halogen-transition metal catalysts were used, to date, only the reactions of Grignard compounds with hydrogen-containing chlorosilanes, described in EP-A-542 250, and the reactions of Grignard compounds with chlorosilanes containing at least three chlorine atoms, described in EP-A-656 363, gave acceptable yields.

SUMMARY OF THE INVENTION

The object of the present invention is to overcome the disadvantages of the prior art and to provide a simple and, in particular, economical process for the preparation of silanes with tertiary hydrocarbon groups in the α-position relative to the silicon atom, starting from halogenosilanes which contain less than three halogen atoms.

DESCRIPTION OF THE PREFERRED EMBODIMENTS

The invention relates to a process for the preparation of silanes of the general formula 1

$$R_m R^1{}_n SiX_{4-m-n} \quad (1)$$

by reaction of Grignard reagents of the general formula 2

$$R^1 MgX^1 \quad (2)$$

with silanes of the general formula 3

$$R_m SiX_{4-m} \quad (3)$$

wherein
   R denotes $C_1$- to $C_{10}$-hydrocarbon radicals optionally substituted by fluorine, chlorine or cyano radicals,
   $R^1$, in the α-position relative to the silicon atom, denotes tertiary $C_4$- to $C_{30}$-hydrocarbon radicals optionally substituted by fluorine, chlorine or cyano radicals,
   X and $X^1$ each denote chlorine, bromine or iodine,
   m denotes the values 2 or 3 and
   n denotes the values 1 or 2,
in the presence of a transition metal catalyst and an inert, aprotic, and chelating compound.

The silanes of the general formula 1 are obtained in high yields and purities. The reaction times are short. Toxicological aspects can easily be taken into consideration when choosing the catalyst and the chelating compound.

Examples of hydrocarbon radicals R are alkyl radicals such as the methyl, ethyl, n-propyl, isopropyl, n-butyl, sec-butyl, and octadecyl radicals; alkenyl radicals such as the vinyl radical; cycloalkyl radicals such as the cyclohexyl radical and methylcyclohexyl radicals; aryl radicals such as the phenyl radical; aralkyl radicals such as the benzyl, phenylethyl, phenylnonyl, and 2-phenylpropyl radicals; and alkaryl radicals such as tolyl radicals.

Examples of substituted hydrocarbon radicals R are, in particular, halogenated hydrocarbon radicals, such as the 3,3,3-trifluoropropyl radical, the 3,3,4,4,5,5,6,6,6-nonafluorohexyl radical and o-, p- and m-chlorophenyl radicals.

Preferred radicals R are $C_1$- to $C_6$-alkyl radicals and phenyl radicals.

$R^1$ is preferably a tertiary hydrocarbon radical of the formula $-CR^2{}_3$, in which the $R^2$ independently of one another have the meanings of R. The radicals $R^2$ are preferably $C_1$- to $C_6$-alkyl radicals, in particular methyl and ethyl radicals, and $C_1$- to $C_6$-alkylenephenyl radicals.

Preferred examples of radicals $R^1$ are the tert-butyl, 1,1-dimethylpropyl and 1,1-diethylpropyl radicals, and the 1,1-dimethyl-2-phenylethyl radical.

Preferred examples of silanes of the general formula 1 are tert-butyldimethylchlorosilane, tert-butyldiethylchlorosilane, tert-butyldi-n-butylchlorosilane, tert-butyl-n-decylmethylchlorosilane, tert-butyl(cyclohexylmethyl)methylchlorosilane, tert-butyldiphenylchlorosilane, tert-butylmethylphenylchlorosilane, 1,1-dimethylbenzyldimethylchlorosilane, and 1,1-dimethylpropyldimethylchlorosilane.

Preferred examples of Grignard reagents of the general formula 2 are tert-butylmagnesium chloride, tert-butylmagnesium bromide, 1,1-dimethylpropylmagnesium chloride, 1,1-diethylpropylmagnesium chloride and 1,1-dimethyl-2-phenylethylmagnesium chloride.

Preferred examples of the silane of the general formula 3 are dimethyldichlorosilane, diethyldichlorosilane, di-n-butyldichlorosilane, -decylmethyldichlorosilane, (cyclohexylmethyl)methyldichlorosilane, diphenyldichlorosilane or ethylphenyldichlorosilane.

Transition metal catalysts which are preferably employed are copper compounds of the 1+ state oxidation such as copper(I) chloride, copper(I) bromide, copper(I) iodide and copper(I) oxide; copper compounds in the 2+ oxidation state such as copper(II) chloride, copper(II) methoxide, copper (II) acetate and copper(II) acetylacetonate; and zinc compounds such as zinc chloride, zinc bromide, zinc acetylacetonate, and zinc chloride-diethyl ether complex.

The additional activation is effected by an inert, aprotic, and chelating compound, which is preferably chosen from glycol ethers, poly(organylamines) or poly (organylphosphanes), and hetero-substituted derivatives thereof. These compounds can be added individually or in mixtures.

The inert, aprotic, chelating glycol ethers used are preferably open chain ethylene glycol di-$C_1$- to $C_2$-alkyl ethers, in particular ethylene glycol di-$C_1$- to $C_6$-alkyl ethers, such as ethylene glycol dimethyl ether, diethylene glycol dimethyl ether, diethylene glycol dibutyl ether, triethylene glycol dimethyl ether, and tetraethylene glycol dimethyl ether, or cyclic ethylene glycol ethers, in particular [12]crown-4 or [18]crown-6.

The inert, aprotic, chelating poly(organylamines) are preferably N,N,N',N'-tetra-$C_1$- to $C_{12}$-alkyl-$C_1$- to $C_3$-alkylenediamines such as N,N,N',N'-tetramethylmethylenediamine, N, N, N', N'-tetramethylethylenediamine and N,N,N',N'-tetraethylethylenediamine, and N,N,N',N',N"-penta-$C_1$- to $C_{12}$-alkyl-$C_1$- to $C_3$-dialkylenetriamines, such as N,N,N',N', N"-pentamethyldiethylenetriamine.

The inert aprotic chelating poly(organylphosphanes) are preferably P,P,P',P'-tetra-$C_1$- to $C_{12}$-alkyl-$C_1$- to $C_3$-alkylenediphosphanes such as P,P,P',P'-tetramethylethylenediphosphane.

In particular, the glycol ethers, poly(organylamines) or poly(organylphosphanes) contain methyl, ethyl, propyl or butyl radicals.

Hetero-substituted derivatives of glycol ethers, poly (organylamines) and poly(organylphosphanes) such as N,N-dimethyl-2-methoxyethylamine, N,N-dimethyl-2-ethoxyethylamine, N,N-dimethyl-3-methoxypropylamine, N,N-dimethyl-3-ethoxypropylamine, and N, N-dimethyl-3-(2-methoxyethoxy)propylamine[2 .2.2]-cryptate, are furthermore claimed.

The Grignard reagent and the silane of the general formula 3 are reacted with one another in a molar ratio of 0.5:1.0 to 1.0:0.5, preferably in a ratio of 1.0:0.8 to 1.0:1.0.

The transition metal catalyst is preferably added in an amount of 0.01 to 10 mol %, based on the Grignard reagent, particularly preferably in an amount of 0.1 to 2 mol %.

The chelating compound is added in an amount of 1–20 equivalents, based on the Grignard reagent, preferably in an amount of 1–8 equivalents. The large excess of the chelating compound serves as a diluent in order to ensure the reaction mixture is easy to stir due to precipitating magnesium halide. Solvents such as, for example, non-polar alkanes and aromatics, are therefore not necessary, but also are not contraindicated.

The reaction is preferably carried out at a temperature from −30° C. to 160° C., particularly preferably 0° C. to 120° C.

The silane of the general formula 1 can optionally be distilled out of the reaction mixture as the pure substance by distillation, or can be distilled as a corresponding solution after addition of a suitable solvent.

The silanes of the general formula 1 are used in particular in the silylation of organic compounds for synthesis purposes, for example for pharmaceuticals, and for analytical purposes.

In the examples described below, all the parts and percentages stated are by weight, unless stated otherwise, and are carried out under the pressure of the surrounding atmosphere, that is to say about 1000 hPa, and at room temperature, that is to say at about 20° C., or at a temperature which is established when the reactants are brought together at room temperature without additional heating or cooling.

EXAMPLE 1

48.6 g (2.0 mol) of magnesium filings and a spatula-tip of iodine are initially introduced into a 2 1 three-necked flask with a precision glass stirrer, straight enclosed-scale thermometer, Dimroth condenser and dropping funnel under a blanket of an inert gas. By addition of 600 ml of ethylene glycol dimethyl ether and 203.7 g (2.2 mol) of tert-butyl chloride, the corresponding Grignard reagent, tert-butylmagnesium chloride, is prepared. Initially 5.2 g (0.02 mol) of copper(II) acetylacetonate and then, at 50° C. over 2 hours, 232.3 g (1.8 mol) of dimethyldichlorosilane are subsequently added dropwise. The internal temperature of the flask rises slightly, and the mixture is subsequently stirred at 70° C. for a further 3 hours to bring the reaction to completion. To remove the precipitated magnesium salt from the solution, the reaction mixture is filtered through a pressure suction filter maintained under an inert atmosphere with argon. The filter cake is rinsed with ethylene glycol dimethyl ether. A concluding fractional distillation of the combined filtrates under normal pressure gives 208.9 g of tert-butyldimethylchlorosilane (77% yield, based on dimethylchlorosilane) as a white crystalline solid in a purity of 95 % (according to $^1$H-NMR).

EXAMPLE 2

Example 1 is repeated with the modification that instead of ethylene glycol dimethyl ether, other inert aprotic chelating glycol ethers are used. The results of these investigations are summarized in Table 1.

TABLE 1

| Glycol ether | Amount employed [ml] | Tert-butyl dimethyl chlorosilane yield [%][1] |
| --- | --- | --- |
| Diethylene glycol dimethyl ether | 800 | 71 |
| Diethylene glycol dibutyl ether | 800 | 67 |
| Triethylene glycol dimethyl ether | 800 | 70 |

[1]yield isolated; content ≧ 95% (according to $^1$H-NMR)

EXAMPLE 3

Example 1 is repeated with the modification that instead of copper(II) acetylacetonate, other transition metal catalysts are used. The results of these investigations are summarized in Table 2.

TABLE 2

| Transition metal catalyst | Amount employed [mol %] | Tert-butyl dimethyl chlorosilane yield [%][1] |
| --- | --- | --- |
| Copper(I) chloride | 1 | 64 |
| Copper(I) chloride | 5 | 65 |
| Copper(I) bromide | 1 | 70 |
| Copper(I) iodide | 1 | 62 |
| Copper(I) oxide | 1 | 27 |
| Copper(II) acetylacetonate | 5 | 77 |

TABLE 2-continued

| Transition metal catalyst | Amount employed [mol %] | Tert-butyl dimethyl chlorosilane yield [%][1] |
|---|---|---|
| Copper(II) chloride | 1 | 69 |
| Copper(II) methoxide | 1 | 68 |
| Copper(II) acetate | 1 | 64 |

[1]yield isolated; content ≧ 95% (according to $^1$H-NMR)

EXAMPLE 4

Example 1 is repeated with the modification that 280.0 g of toluene are added to the filtrate in order to obtain a toluene solution instead of the pure substance in the subsequent working up by distillation. 440.0 g of a toluene solution of tert-butyldimethylchlorosilane with a tert-butyldimethylchlorosilane content of 50% by weight are distilled off. This corresponds to a tert-butyldimethylchlorosilane yield of 81%, based on dimethyldichlorosilane.

EXAMPLE 5

48.6 g (2.0 mol) of magnesium filings and a spatula-tip of iodine are initially introduced into a 2 l three-necked flask with a precision glass stirrer, straight enclosed-scale thermometer, Dimroth condenser and dropping funnel under a blanket of inert gas. By addition of 600 ml of ethylene glycol dimethyl ether and 203.7 g (2.2 mol) of tert-butyl chloride, tert-butylmagnesium chloride is prepared. Initially 5.2 g (0.02 mol) of copper(II) acetylacetonate and then, at 50° C. over 2 hours, 455.8 g (1.8 mol) of diphenyldichlorosilane are subsequently added dropwise. The internal temperature of the flask rises slightly, and the mixture is subsequently stirred at 70° C. for a further 3 hours to bring the reaction to completion. To remove the precipitated magnesium salt from the solution, the reaction mixture is filtered through a pressure suction filter maintained under an argon atmosphere. The filter cake is rinsed with ethylene glycol dimethyl ether. A concluding fractional distillation of the combined filtrates in vacuo gives 420.6 g of tert-butyldiphenylchlorosilane (85% yield, based on the diphenyldichlorosilane) as a colorless liquid in a GC purity of 92%.

What is claimed is:

1. A process for the preparation of a silane of the general formula 1

$$R_m R^1{}_n SiX_{4-m-n} \quad (1)$$

by reaction of a Grignard reagent of the general formula 2

$$R^1 MgX^1 \quad (2)$$

with a silane of the general formula 3

$$R_m SiX_{4-m} \quad (3)$$

wherein

R denotes $C_1$- to $C_{10}$-hydrocarbon radicals optionally substituted by fluorine, chlorine or cyano radicals, $R^1$, in the α-position relative to the silicon atom, denotes tertiary $C_4$- to $C_{30}$-hydrocarbon radicals optionally substituted by fluorine, chlorine or cyano radicals, X and $X^1$ each denote chlorine, bromine or iodine, m denotes the values 2 or 3 and n denotes the values 1 or 2, in the presence of a transition metal catalyst and an inert, aprotic, and chelating compound.

2. A process as claimed in claim 1, in which $R^1$ is a tertiary hydrocarbon radical of the formula —$CR^2{}_3$, in which the $R^2$ denotes $C_1$- to $C_6$-alkyl radicals or $C_1$- to $C_6$-alkylenephenyl radicals.

3. A process as claimed in claim 1, in which the radicals R are $C_1$- to $C_6$-alkyl radicals or phenyl radicals.

4. A process as claimed in claim 2, in which the radicals R are $C_1$- to $C_6$-alkyl radicals or phenyl radicals.

5. A process as claimed in claim 1, in which a copper compound in the 1+ oxidation state, a copper compound in the 2+ oxidation state, or a zinc compound is employed as the transition metal catalyst.

6. A process as claimed in claim 2, in which a copper compound in the 1+ oxidation state, a copper compound in the 2+ oxidation state, or a zinc compound is employed as the transition metal catalyst.

7. A process as claimed in claim 3, in which a copper compound in the 1+ oxidation state, a copper compound in the 2+ oxidation state, or a zinc compound is employed as the transition metal catalyst.

8. A process as claimed in claim 4, in which a copper compound in the 1+ oxidation state, a copper compound in the 2+ oxidation state, or a zinc compound is employed as the transition metal catalyst.

9. A process as claimed in claim 1, in which the inert, aprotic, and chelating compound comprises a glycol ether, a poly(organylamine), a poly(organylphosphane), a heterosubstituted derivative thereof, and mixtures thereof.

10. A process as claimed in claim 2, in which the inert, aprotic, and chelating compound comprises a glycol ether, a poly(organylamine), a poly(organylphosphane), a heterosubstituted derivative thereof, and mixtures thereof.

11. A process as claimed in claim 3, in which the inert, aprotic, and chelating compound comprises a glycol ether, a poly(organylamine), a poly(organylphosphane), a heterosubstituted derivative thereof, and mixtures thereof.

12. A process as claimed in claim 4, in which the inert, aprotic, and chelating compound comprises a glycol ether, a poly(organylamine), a poly(organylphosphane), a heterosubstituted derivative thereof, and mixtures thereof.

13. A process as claimed in claim 5, in which the inert, aprotic, and chelating compound comprises a glycol ether, a poly(organylamine), a poly(organylphosphane), a heterosubstituted derivative thereof, and mixtures thereof.

14. A process as claimed in claim 6, in which the inert, aprotic, and chelating compound comprises a glycol ether, a poly(organylamine), a poly(organylphosphane), a heterosubstituted derivative thereof, and mixtures thereof.

15. A process as claimed in claim 7, in which the inert, aprotic, and chelating compound comprises a glycol ether, a poly(organylamine), a poly(organylphosphane), a heterosubstituted derivative thereof, and mixtures thereof.

16. A process as claimed in claim 8, in which the inert, aprotic, and chelating compound comprises a glycol ether, a poly(organylamine), a poly(organylphosphane), a heterosubstituted derivative thereof, and mixtures thereof.

17. The process of claim 1, wherein said inert, aprotic, chelating compound is a cyclic ethylene glycol ether or an ethylene glycol di-$C_1$- to $C_{12}$-alkyl ether, or mixture thereof.

18. The process of claim 1, wherein said inert, aprotic, chelating compound is selected from the groups consisting of [12]crown-4; [18]crown-6; N,N,N',N'-tetra-$C_1$- to $C_{12}$- alkyl-$C_1$- to $C_3$-alkylenediamines; N,N,N',N',N"-penta-$C_1$- to $C_{12}$-alkyl-$C_1$- to $C_3$-dialkylenetriamines; P,P,P',P'-tetra-$C_1$- to $C_{12}$-alkyl-$C_1$- to $C_3$-alkylenediphosphanes; N,N-dimethyl-2-methoxyethylamine; N,N-dimethyl-2-ethoxyethylamine; N,N-dimethyl-3-methoxypropylamine; N,N-dimethyl-3-ethoxypropylamine; and N,N-dimethyl-3-(2-methoxyethoxy)propylamine[2.2.2]-cryptate, and mixtures thereof.

19. A process for the preparation of a silane of the general formula 1

$$R_mR^1_nSiX_{4-m-n} \quad (1)$$

by reaction of a Grignard reagent of the general formula 2

$$R^1MgX^1 \quad (2)$$

with a silane of the general formula 3

$$R_mSiX_{4-m} \quad (3)$$

wherein
R denotes $C_1$- to $C_{10}$-hydrocarbon radicals optionally substituted by fluorine, chlorine or cyano radicals,
$R^1$, in the α-position relative to the silicon atom, denotes tertiary $C_4$- to $C_{30}$-hydrocarbon radicals optionally substituted by fluorine, chlorine or cyano radicals,
X and $X^1$ each denote chlorine, bromine or iodine,
m is 2 or 3 and
n is 1 or 2,
in the presence of a transition metal catalyst and an inert, aprotic, and chelating compound selected from the group consisting of N-alkyl substituted poly(organylamines) and P-alkyl substituted poly(organylphosphanes).

20. A process for the preparation of a silane of the general formula 1

$$R_mR^1_nSiX_{4-m-n} \quad (1)$$

by reaction of a Grignard reagent of the general formula 2

$$R^1MgX^1 \quad (2)$$

with a silane of the general formula 3

$$R_mSiX_{4-m} \quad (3)$$

wherein
R denotes $C_1$- to $C_{10}$-hydrocarbon radicals optionally substituted by fluorine, chlorine or cyano radicals,
$R^1$, in the α-position relative to the silicon atom, denotes tertiary $C_4$- to $C_{30}$-hydrocarbon radicals optionally substituted by fluorine, chlorine or cyano radicals,
X and $X^1$ each denote chlorine, bromine or iodine,
m is 2 or 3 and
n is 1 or 2,
in the presence of a transition metal catalyst and an inert, aprotic, and chelating compound selected from the group consisting of ethylene glycol di-$C_1$- to $C_{12}$-alkyl ethers, triethylene glycol dimethyl ether, tetraethylene glycol dimethyl ether, cyclic ethylene glycol ethers, and mixtures thereof.

* * * * *